United States Patent
Armitstead et al.

(10) Patent No.: US 10,863,949 B2
(45) Date of Patent: Dec. 15, 2020

(54) DISCRIMINATION OF CHEYNE-STOKES BREATHING PATTERNS

(71) Applicant: ResMed Pty Ltd, Bella Vista (AU)

(72) Inventors: Jeffrey Peter Armitstead, North Sydney (AU); Dinesh Ramanan, Telopea (AU)

(73) Assignee: ResMed Pty Ltd

( * ) Notice: Subject to any disclaimer, the term of this patent is extended or adjusted under 35 U.S.C. 154(b) by 1184 days.

(21) Appl. No.: 14/374,761

(22) PCT Filed: Jan. 25, 2013

(86) PCT No.: PCT/AU2013/000063
§ 371 (c)(1),
(2) Date: Jul. 25, 2014

(87) PCT Pub. No.: WO2013/110136
PCT Pub. Date: Aug. 1, 2013

(65) Prior Publication Data
US 2015/0038867 A1 Feb. 5, 2015

Related U.S. Application Data

(60) Provisional application No. 61/591,346, filed on Jan. 27, 2012.

(51) Int. Cl.
*A61B 5/08* (2006.01)
*A61B 5/00* (2006.01)
(Continued)

(52) U.S. Cl.
CPC ............ *A61B 5/7282* (2013.01); *A61B 5/087* (2013.01); *A61B 5/0816* (2013.01);
(Continued)

(58) Field of Classification Search
CPC ..... A61B 7/003; A61B 5/0816; A61B 5/0826; A61B 5/4818
See application file for complete search history.

(56) References Cited

U.S. PATENT DOCUMENTS

| | | |
|---|---|---|
| 5,398,682 A | 3/1995 | Lynn |
| 5,605,151 A | 2/1997 | Lynn |

(Continued)

FOREIGN PATENT DOCUMENTS

| | | |
|---|---|---|
| CN | 101087559 A | 12/2007 |
| DE | 102008061122 A1 | 6/2010 |

(Continued)

OTHER PUBLICATIONS

Gerhard Weinreich et al. "Validation of ApneaLink as screening device for Cheyne-Stokes respiration .", Sleep, vol. 32, No. 4, Apr. 1, 2009 (Apr. 1, 2009), pp. 553-557, XP055078483, ISSN: 0161-8105 * the whole document *.

(Continued)

*Primary Examiner* — Puya Agahi
(74) *Attorney, Agent, or Firm* — Botos Churchill IP Law LLP

(57) ABSTRACT

A method of a processor for detecting a presence of Cheyne-Stokes respiration from a respiration signal includes accessing data representative of a respiration signal. Data is assessed to detect apnea and/or hypopnea events. A cycle length histogram is determined based on the events and an incident of Cheyne-Stokes respiration is detected based on the cycle length histogram.

26 Claims, 9 Drawing Sheets

(51) Int. Cl.
*A61M 16/00* (2006.01)
*A61B 5/087* (2006.01)
*A61B 5/091* (2006.01)
*A61M 16/06* (2006.01)

(52) U.S. Cl.
CPC ............ *A61B 5/0826* (2013.01); *A61B 5/091* (2013.01); *A61B 5/7275* (2013.01); *A61M 16/0003* (2014.02); *A61M 16/0069* (2014.02); *A61M 16/026* (2017.08); *A61B 5/4818* (2013.01); *A61M 16/0666* (2013.01); *A61M 2016/003* (2013.01); *A61M 2016/0033* (2013.01); *A61M 2205/3303* (2013.01); *A61M 2205/52* (2013.01); *A61M 2230/005* (2013.01); *A61M 2230/205* (2013.01); *A61M 2230/40* (2013.01)

(56) References Cited

U.S. PATENT DOCUMENTS

| | | |
|---|---|---|
| 5,891,023 A | 4/1999 | Lynn |
| 6,138,675 A | 10/2000 | Berthon-Jones |
| 6,223,064 B1 | 4/2001 | Lynn et al. |
| 6,748,252 B2 | 6/2004 | Lynn et al. |
| 6,760,608 B2 | 7/2004 | Lynn |
| 7,081,095 B2 | 7/2006 | Lynn et al. |
| 7,094,207 B1 | 8/2006 | Koh |
| 7,361,146 B1 | 4/2008 | Bharmi et al. |
| 7,398,115 B2 | 7/2008 | Lynn |
| 7,413,549 B1 | 8/2008 | Koh |
| 7,758,503 B2 | 7/2010 | Lynn et al. |
| 8,241,213 B2 | 8/2012 | Lynn et al. |
| 8,666,467 B2 | 3/2014 | Lynn et al. |
| 2002/0190863 A1 | 12/2002 | Lynn |
| 2004/0059240 A1 | 3/2004 | Cho et al. |
| 2004/0134496 A1 | 7/2004 | Cho et al. |
| 2005/0101833 A1 | 5/2005 | Hsu et al. |
| 2005/0119711 A1* | 6/2005 | Cho .................... A61B 5/0205 607/42 |
| 2006/0070624 A1 | 4/2006 | Kane et al. |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0235324 A1 | 10/2006 | Lynn |
| 2007/0073181 A1 | 3/2007 | Pu et al. |
| 2007/0093721 A1 | 4/2007 | Lynn et al. |
| 2008/0177195 A1* | 7/2008 | Armitstead ............ A61B 5/087 600/529 |
| 2008/0287756 A1 | 11/2008 | Lynn |
| 2010/0018530 A1* | 1/2010 | Schindhelm ............ G06F 19/00 128/204.23 |
| 2010/0079292 A1 | 4/2010 | Lynn et al. |
| 2010/0174341 A1* | 7/2010 | Bolea .................. A61N 1/3601 607/42 |
| 2010/0234705 A1 | 9/2010 | Lynn |
| 2010/0307500 A1 | 12/2010 | Armitstead |
| 2011/0054279 A1 | 3/2011 | Reisfeld et al. |
| 2011/0066059 A1* | 3/2011 | Lehrman .................. A61B 5/08 600/529 |
| 2011/0208539 A1 | 8/2011 | Lynn |
| 2011/0301472 A1 | 12/2011 | Grober et al. |
| 2012/0016218 A1 | 1/2012 | Lau et al. |
| 2012/0302845 A1 | 11/2012 | Lynn et al. |
| 2013/0060110 A1 | 3/2013 | Lynn et al. |
| 2013/0158375 A1 | 6/2013 | Lynn |

FOREIGN PATENT DOCUMENTS

| | | |
|---|---|---|
| WO | 2006047826 A1 | 5/2006 |
| WO | 2006066337 A1 | 6/2006 |
| WO | 2009118737 A2 | 10/2009 |
| WO | 2010121290 A1 | 10/2010 |

OTHER PUBLICATIONS

Supplementary European Search Report for Application No. EP13741408 dated Aug. 14, 2015.
G.Weinreich et al, 'Validation of ApneaLink as Screening Device for Cheyne-Stokes Respiration', Sleep, 2009, vol. 32, No. 4, pp. 553-557, pp. 554-555; Figs 3 and 4.
International Search Report for Application No. PCT/AU2013/000063 dated May 3, 2013.
Written Opinion of the International Searching Authority for Application No. PCT/AU2013/000063 dated Jan. 22, 2014.
Written Opinion of the International Searching Authority for Application No. PCT/AU2013/000063 dated May 3, 2013.

\* cited by examiner

DISCRIMINATION OF CHEYNE-STOKES BREATHING PATTERNS

CROSS-REFERENCES TO RELATED APPLICATIONS

The present application is a national phase entry under 35 U.S.C. § 371 of International Application No. PCT/AU2013/000063, filed Jan. 25, 2013, published in English, which claims priority from U.S. Provisional Patent Application No. 61/591,346, filed Jan. 27, 2012, all of which are hereby incorporated herein by reference.

FIELD OF THE TECHNOLOGY

The present technology relates to the discrimination of breathing abnormalities by analysis of physiological signal(s). In particular, the technology relates to the discrimination of Cheyne-Stokes respiration ("CSR") by the analysis of a respiratory flow signal. The technology may also relate to the training of a classifier able to provide probability values for CSR discrimination.

BACKGROUND OF THE TECHNOLOGY

Cheyne-Stokes Respiration ("CSR") is a waxing-and-waning pattern of breathing experienced by some patients when asleep. Typically, these patients have heart failure or have suffered a brain stem lesion (i.e., stroke). The pattern may be caused by a combination of (i) excessive delay of the signals from the blood gas receptors to the respiratory centre and (ii) excessive 'loop' gain, a combination of plant gain and controller gain.

It can be useful to know if subjects on continuous positive airway pressure (CPAP) therapy are exhibiting CSR because there is a potential for improved therapy with, for example, an adaptive support ventilator (ASV) device. Alternatively, the subject can be monitored to see if the CSR persists or whether it was a result of so-called CPAP-emergent central sleep apnea (CSA). The 'clinical significance' of CSR is substantial and it is important to know how much CSR is present during sleep.

The diagnosis of CSR usually involves conducting a sleep study, and analyzing the resulting polysomnography ("PSG") data. In a full diagnostic PSG study, a range of biological parameters are monitored that typically include a nasal flow signal, measures of respiratory effort, pulse oximetry, sleeping position, and may include: electroencephalography ("EEG"), electrocardiography ("ECG"), electromyography ("EMG") and electro-oculography ("EOG"). Breathing characteristics are also identified from visual features, thus allowing a clinician to assess respiratory function during sleep and evaluate any presence of CSR.

While the examination by a clinician is the most comprehensive method, it is a costly process and depends heavily upon clinical experience and understanding. For efficient screening of patients, a classifier algorithm has been developed by the assignee of this application that automates the scoring process by calculating the probability of CSR occurring based on a nasal flow signal. The method is disclosed in U.S. patent application Ser. No. 11/576,210 (U.S. Patent App. Pub. No. 20080177195) filed Mar. 28, 2007, and published as WO2006066337A1 Jun. 29, 2006. The method may include a flow-based classifier where a probability of CSR is calculated given a sequence of discrete flow values.

The concept of a classifier is common to many fields where it is desirable to assign an object or an underlying state of an object to one of a number of classes. This concept is used, for example, in the fields of voice recognition (where sound bytes are classified as different words or syllables), radar detection (where visual signals are classified as enemy/friendly targets) and medical diagnosis (where test results are used to classify a patient's disease state). The design of a classifier falls under the field of Pattern Recognition and a classifier can be of the supervised type (the classifier is built from training data which has been pre-classed by a supervisor or "expert") or unsupervised type (where the natural ordering or clustering of the data determines the different classes). Time signal classification usually relies on representing the signal at particular time points with "features". Features are simply numbers that distil the essence of the signal at a point in time, a form of compression. A set (or vector) of features is called a "pattern". A classifier takes a pattern and manipulates it mathematically with a suitable algorithm to produce a probability value for each of a number of classes. The pattern is assigned to the class with the highest probability.

The algorithm described in WO2006066337A1 uses multidimensional feature space and performs cluster analysis by using discriminant functions to separate the features into clusters. This approach is computationally intensive and is typically performed on a separate computer.

SUMMARY OF THE TECHNOLOGY

A signal representative of respiration, such as a nasal flow signal, an oximetry signal or the like, may be recorded from a patient using a logging device which includes a data-acquisition system and a memory. The respiratory signal may be processed in real time either on-board by the recording device or off-line using a computer or processor with the disclosed methodologies.

The technology may provide a method of a processor for indicating a presence of Cheyne-Stokes respiration from a respiration signal and may include the steps of accessing respiratory data representative of the respiration signal and assessing the accessed data to detect apnea and/or hypopnea events. A cycle length histogram may be generated based on the events. An incident of Cheyne-Stokes respiration may be detected based on the generated cycle length histogram.

In some embodiments, the cycle length histogram includes a plurality of bins, each of the plurality of bins having a midpoint and a bin width. The plurality of bins may be evenly spaced. Assessing the data to detect apnea and/or hypopnea events may include determining the duration of each event. Detecting an incident of Cheyne-Stokes respiration may include calculating power over a combination of bins covering a select set of cycle lengths. The method may further include evaluating respiratory data directly following the apnea or the hypopnea events to estimate a shape feature representing change in the respiratory data, wherein detecting an incident of Cheyne-Stokes respiration is based on both the cycle length histogram and the estimated shape feature. The respiratory data may include values of at least one of respiratory flow, ventilation and/or tidal volumes. The respiratory flow data may specifically include data of respiratory flow peaks.

In another aspect, an apparatus for indicating a presence of Cheyne-Stokes respiration from a respiration signal may include a memory for storing the respiration signal, a processor, coupled with the memory, the processor being configured (a) to assess the data to detect apnea and/or hypopnea events, (b) to generate a cycle length histogram based on the events, and (c) to detect an incident of Cheyne-Stokes respiration based on the cycle length histogram.

In some embodiment, the processor may be further configured to evaluate a respiratory signal directly following apnea or hypopnea events to estimate a shape feature representing change in the peaks of the flow data and to detect an incident of Cheyne-Stokes respiration based on both the cycle length histogram and the estimated shape feature. The processor may be further configured to evaluate at least one of values of the respiratory flow peaks or values of the tidal volumes of the respiratory signal.

In another aspect, a method of a processor for indicating a presence of Cheyne-Stokes respiration from a respiration signal may include accessing respiratory flow data representative of the respiration signal, assessing the accessed respiratory data to detect apnea and/or hypopnea events, evaluating respiratory data directly following the apnea or the hypopnea events to estimate a shape feature representing change in the peaks of the flow data, and detecting an incident of Cheyne-Stokes respiration based on the estimated shape feature.

In some embodiments, the evaluating step may include calculating the inspiratory tidal volumes during at least a portion of the time between two adjacent apnea and/or the hypopnea events. It may also include calculating the product of the peak inspiratory flow data and inspiratory tidal volume and storing them in a morphology vector. It may also include calculating the expiratory tidal volumes and/or peak expiratory flow. Alternatively, it may not use such breath-by-breath features and instead involve calculating a ventilation signal by integrating the respiratory flow signal and storing it in a morphology vector. Evaluating respiratory data may further include computing a mean squared error between the morphology vector and an approximating function. Such a calculation gives an indication of the overall shape of the ventilation drive (as well as of the equivalent respiratory flow) and constitutes a shape feature. The method may further include determining a cycle length histogram based on the events And wherein detecting an incident of Cheyne-Stokes respiration is based on both the cycle length histogram and the shape feature.

In another aspect, an apparatus for indicating a presence of Cheyne-Stokes respiration from a respiratory data associated with a respiration signal, the apparatus may include a memory for storing the respiratory data, and a processor, coupled with the memory, the processor being configured to (a) assess the respiratory data to detect apnea and/or hypopnea events, (b) evaluate features in the respiratory data directly following the apnea or the hypopnea events to estimate a shape feature representing a change in the peaks of the flow data such as, for example, a rise and/or fall of the patient's breathing drive, and (c) detect an incident of Cheyne-Stokes respiration based on the estimated shape feature.

In some embodiment, the processor may be configured for calculating peak inspiratory flow data and inspiratory tidal volume, wherein evaluating features of the flow data includes calculating the product of the peak inspiratory flow data and inspiratory tidal volume and storing them in a morphology vector. The processor may be configured to evaluate features of the flow data by computing a mean squared error between the morphology vector and an approximating function. The processor may also be configured to normalize the morphology vector by converting it into 0 to 1 probability spaces.

In another aspect, a method of a processor for indicating a presence of Cheyne-Stokes respiration from a respiration signal may include accessing respiratory data representative of the respiration signal, assessing the respiratory data to detect apnea and/or hypopnea events, determining a cycle length histogram based on the events, evaluating features of the respiratory flow data directly following the apnea or the hypopnea events to estimate a shape feature representing change in the peaks of the flow data such as, for example, a rise and/or fall of the patients breathing drive, and detecting an incident of Cheyne-Stokes respiration based on the cycle length histogram and the estimated shape feature.

In some embodiment, the method may further include normalizing the cycle length histogram and the shape feature by converting them into 0 to 1 probability spaces. Assessing the data to detect apnea and/or hypopnea events may include calculating the duration of at least one apneic period and at least one cycle length and further including calculating a duty cycle based on the duration of the at least one apneic period and the at least one cycle length. Detecting an incident of Cheyne-Stokes respiration may include calculating power over a combination of bins (of the cycle length histogram) covering a select set of cycle lengths. Detecting an incident of Cheyne-Stokes respiration may include determining the Cheyne-Stokes respiration probability using the shape feature, cycle length and the power. The method may further include determining an overall Cheyne-Stokes respiration probability over an entire sleep period by combining weighted Cheyne-Stokes respiration probability for multiple selected periods.

In another aspect, an apparatus for indicating a presence of Cheyne-Stokes respiration from a respiration signal, the apparatus may include a memory for storing, respiratory data associated with the respiration signal, a processor, coupled with the memory, the processor being configured to: (a) assess the respiratory data to detect apnea and/or hypopnea events, (b) determine a cycle length histogram based on the events, (c) evaluate features of the respiratory data directly following the apnea or the hypopnea events to estimate a shape feature representing change in the respiratory data such as, for example, a rise and/or fall of the patients breathing drive, and (d) detect an incident of Cheyne-Stokes respiration based on the cycle length histogram and the estimated shape feature.

In some embodiments, the processor may assess the data to detect apnea and/or hypopnea events by calculating the duration of at least one apneic period and at least one cycle length and the processor is further configured to calculate a duty cycle based on the duration of the at least one apneic period and the at least one cycle length. The processor may be configured to detect an incident of Cheyne-Stokes respiration by calculating power over a combination of bins covering a select set of cycle lengths and determining the Cheyne-Stokes respiration probability using the shape feature, cycle length and the power.

In another aspect, an apparatus to detect. CSR from a respiration signal may include a controller having at least one processor to access respiratory data representing a respiration signal, the controller being further configured to: assess the respiratory data to detect apnea and/or hypopnea events, (b) determine a cycle length histogram based on the events, (c) evaluate respiratory data directly following the apnea or the hypopnea events to calculate a shape feature representing a change in the respiratory data such as, for example, a rise and/or fall of the patients breathing drive, and (d) detect an incident of Cheyne-Stokes respiration based on the cycle length histogram and the shape feature.

In some embodiments, the calculation of the shape feature may be based on at least one of values, of the respiratory flow peaks or values of the tidal volumes or values of ventilation. It should be noted that the ventilation and the tidal volume data may be calculated based on the respiratory flow data. Thus, the processing arrangement may be such that, instead of receiving directly ventilation and/or tidal volume data, the controller may receive respiratory flow data and, on the basis of this respiratory flow data, calculate the ventilation and the tidal volume data used in estimating the shape feature.

The apparatus may further include a flow sensor, wherein the controller is further configured to determine the respiration signal with the flow sensor. The apparatus may further include a flow generator configured to produce a breathable gas for a patient at a pressure above atmospheric pressure, wherein the controller is further configured to control the flow generator to produce the breathable gas according to a pressure therapy regime based on the detected hypopnea.

Other features of the technology will be apparent from consideration of the information contained in the following detailed description, abstract and claims.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

Figure 1:
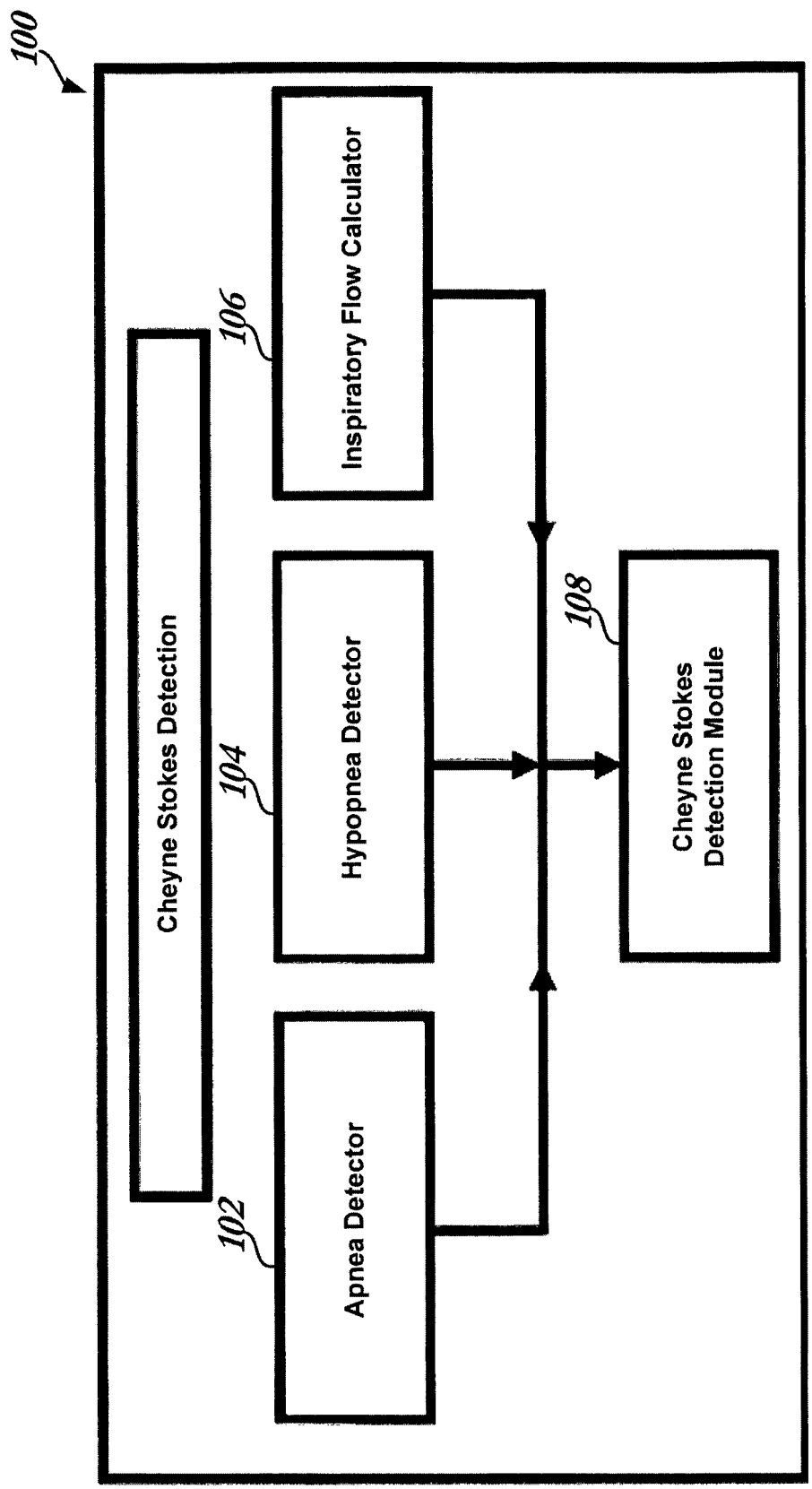
FIG. 1 is a structural diagram of an example CSR detector of some embodiments of the present technology.

Embodiments of the present technology may include a system, device, classifier, and/or methods with CSR event detection. Example embodiments are herein described with reference to the accompanying drawings and more specifically FIGS. 1-7.

CSR is a form of periodic breathing believed to be caused by instability in the central nervous system control of ventilation. The breathing pattern in a CSR sufferer is characterized by a "waxing and waning" tidal volume as respiration alternates between repetitive episodes of apnea/hypopnea and hyperpnea. Recordings of nasal flow signals in a compressed time scale reveal a pattern that is similar to an Amplitude-Modulated ('AM') waveform.

Cheyne-Stokes Respiration (CSR) may be observed through direct measurement of pulmonary functions such as a nasal flow recording or airway flow recording. Due to the coupling between the cardiac and pulmonary system, CSR may also be identified as alternating periods of desaturation and resaturation through an oximetry signal. Thus, oximetry signals may provide a source of information available for the analysis of Cheyne-Stokes breathing. Benefits of this approach may include the use of oximeters for non-invasively measuring blood oxygen saturation levels, which is a determinant of a subject's health condition. Additional information on obtaining a signal via oximetry can be found in International Patent Application No. PCT/AU2010/000416, filed Apr. 15, 2010, entitled "Discrimination of Cheyne-Stokes Breathing Patterns By Use of Oximetry Signals," the contents of which are hereby incorporated by reference in its entirety. Oximetry recordings may provide evidence of the occurrence of CSR or other breathing abnormalities (e.g., Obstructive Sleep Apnea). Thus, a successful algorithm will be able to discriminate between the different breathing disorders:

The present technology implements a processor, for example in a flow generator, to detect CSR by analyzing a signal representative of patient respiration, including the apneas and/or hypopneas occurring during a sleep period. Patients with CSR will have clearly distinguishable clusters of apneas and/or hypopneas with certain characteristics that allow determination to be made whether the apnea and/or hypopneas clusters can be identified as CSR.

One feature that may be relevant in examining the clusters of apneas and/or hypopneas in a breathing pattern is the cycle length, which may be considered to be the time separating two adjacent apneas and/or hypopneas. Thus, the cycle length may be measured as the time from start of one apnea and/or hypopnea to the start of the next successive apnea and/or hypopnea. Alternatively, the cycle length may be defined as the time from the end of one apnea and/or hypopnea to the end of the next successive apnea and/or hypopnea. Typically, the cycle length of the apnea and/or hypopnea for patients with CSR will vary between 40 and 90 seconds. Thus, by comparing the cycle lengths of the breathing patterns of a patient with a typical cycle length associated with CSR, a conclusion may be made whether the patient suffers from CSR. It may be noted that the difference between two start or end apnea and/or hypopnea markers is only one possible way to calculate cycle length. Other equivalent time points can also be used to calculate the cycle length—i.e. the time between the n-th seconds of two adjacent apneas can be used, when n could be any real number. More obvious examples include the case where n is an integer-say between 1 and 30, such as 10. Alternatively, cycle length may be calculated as the time between the peaks of the respiratory flow signal between two hyperpneas (the period of breathing between two successive apnea and/or hypopnea events).

Another characteristic of CSR periods is hyperpnoea periods which contain large breaths flanked by smaller breaths. This and other morphology related features (also referred to as shape features) will be discussed in more detail, below, with reference to FIGS. 5A and 5B. By extracting and analysing such morphology patterns, one or more shape features can be classified to detect CSR.

To begin the analysis, a signal representative of respiration, such as a nasal flow signal from a flow sensor, an oximetry signal from a pulse oximeter or the like, may be first recorded from a patient using a logging device. The recorded signal may be referred to as the raw or collected respiration flow signal. In some embodiments, the signal may be framed into different breaths by a breath framer. The framed signal may then proceed to a set of detectors.

Detectors

FIG. 1 illustrates a CSR detector 100 having several detecting and calculating components and their relationship to an example Cheyne-Stokes detection module. The plurality of components may be implemented by one or more processors in a device or apparatus such as a respiratory treatment apparatus with a flow generator or other separate computing or detection devices. The components may access the data representative of a patient respiration signal and assess the data to determine the presence of a breathing-related event.

The plurality of detecting components may include an apnea detector 102. The apnea detector 102 accesses and assesses the respiration flow signal to detect apnea events. For example, if an apneic period appears, it may generate a flag when the apnea ends. The apnea detector 102 may calculate the duration of the apnea. Thus, the apnea detector 102 is configured to provide data on the presence and duration of clusters of apneas to other modules or processes. Methods for detection of apnea may be those known in the art, such as, the methodologies described in U.S. Pat. No. 6,138,675.

The detector components may also include a hypopnea detector 104. The hypopnea detector 104 may evaluate the respiration signal and detect incidents of hypopnea. For example, if a hypopneic period is detected, it may generate a flag when the hypopnea ends. The hypopnea detector 104 may also calculate the duration of the detected hypopnea. The hypopnea detector 104 may be in communication with other modules or process to provide data on the presence of hypopnea clusters and their durations. Known methodologies in the art may be implemented for hypopnea detection. For example, the methods described in U.S. patent application Ser. No. 12/781,070 filed on May 17, 2010 the disclosure of which is incorporated herein by reference.

An inspiratory flow calculator 106 may also be included that examines the inspiratory part of a breath and calculates various respiratory features that may be associated with the inspiratory flow. Examples of inspiratory flow associated features may include, but are not limited to, inspiratory time, tidal volume and peak flow. The inspiratory flow calculator may calculate any or all of these features. In the exemplary methodology described herein, the tidal volume and peak flow are determined by the inspiratory flow calculator. These features may be input to the next module or process for further processing and/or classification. Similar processing and classification may be performed also based on the expiratory portion of the respiratory signal. Optionally, a ventilation signal may be calculated by integrating the respiratory flow data. This signal can also then be used as an input in the next module.

Example Cheyne-Stokes Detection Module

The data outputs from the detectors 102, 104 and the calculator 106 are passed to the Cheyne-Stokes detection module 108, which classifies a period of Cheyne-Stokes respiration by analyzing clusters of Apneas and Hypopneas. Specifically, the Cheyne-Stokes detection module may calculate one or more raw features based on the collected data set, classify them and then generate the output indicative of CSR detection. For ease of illustration, the raw features will be described with reference to FIG. 2, which illustrates a typical CSR period.

As discussed, the apnea detector 102, hypopnea detector 104 and inspiratory flow calculator 106 provide data on the presence of apneas and hypopneas, such as the duration of each, and inspiratory flow features. From these parameters, the Cheyne-Stokes detection module may calculate three raw features: (1) a cycle length histogram for a cluster of apneas and/or hypopneas, (2) shape feature and (3) duty cycle. These three raw features will be discussed in turn.

Figure 2:
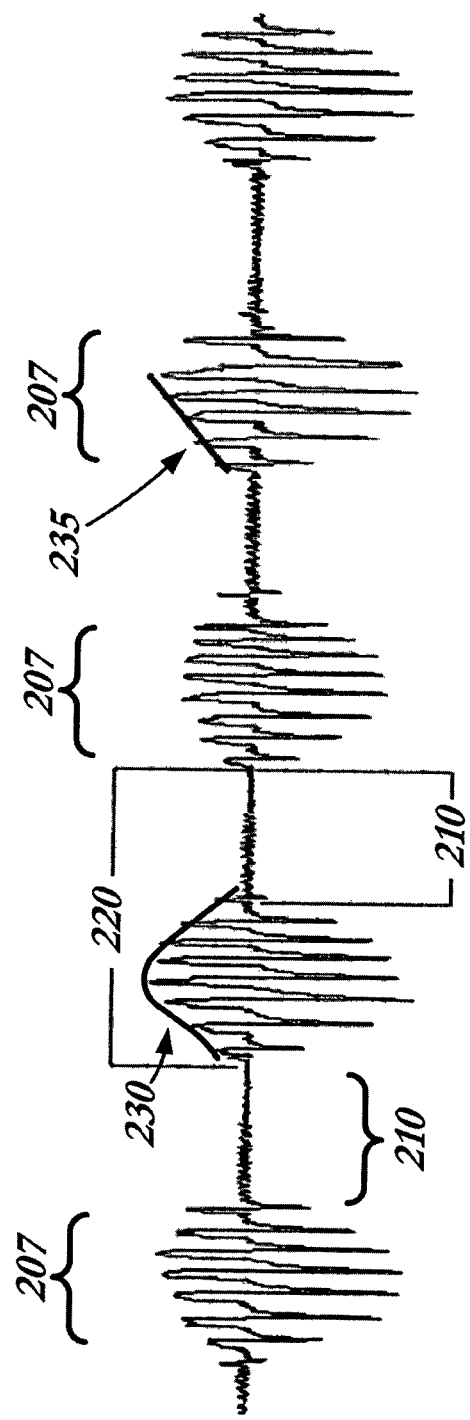
FIG. 2 shows a respiratory flow waveform comprising periodic waxing and waning and characterizing a typical CSR period.

As shown in FIG. 2, during a typical CSR period, there may be a periodic waxing and waning of breathing. That is to say that a length of apnea 210 will occur in regular succession and will be separated by periods of respiration where the breathing drive will slowly come and go. This is shown in FIG. 2 as breaths having a large magnitude, being flanked by breaths with a small magnitude during a hyperpnea 207. The cycle length 220 may be defined as the elapsed time between the start time (or end time) of either two successive apneas 210 or two successive hyperpneas 207. Thus, the first useful raw feature is the cycle length, which may be calculated using the data on apnea and hypopnea clusters and durations. This information will be further processed using a cycle length histogram and compared to the typical cycle length for a CSR subject.

Data may also be gathered concerning the return of breathing drive following an apnea 210. Thus, a second useful raw feature that reflects this return is the "shape feature". Specifically, the shape feature captures at least a portion or the overall profile 230 of the breathing drive. The overall drive 230 is characterised by a return of the breathing drive after an apnea or hypopnea and a subsequent reduction of the breathing drive leading to a subsequent apnea or hypopnea. One example of a shape feature is the jump feature 235, which describes the amplitude change in the "jump" of peak flows in the increasing portion of the breathing drive. The jump feature 235 is illustrated in FIG. 2 with a diagonal line tracking a plurality of respiratory flow peaks and marking increased breathing drive during hyperapnea. The flow peaks for which the profile is determined may be adjacent or non-adjacent. Thus, following an apnea, a shape feature, for example in the form of jump feature 235, can be calculated to evaluate the return to normal breathing. Alternatively, the shape feature may be calculated based on other portions of, or on the entire breathing profile 230.

Specifically, the jump feature 235 attempts to quantify the manner in which the breathing drive returns. Following an obstructive apnea and/or hypopnea, one would expect the breathing drive to return extremely quickly and in a large way. Following a central apnea and/or hypopnea, the breathing drive will return more gradually.

A third useful raw feature is the duty cycle. Using the apnea length 210 and the cycle length 220, the duty cycle may also be calculated. The duty cycle may be defined as the apnea length 210 divided by the cycle length 220. For a CSR patient, the duty cycle is expected to be about ⅓.

Thus, for each of the raw features, the Cheyne-Stokes detection module 108 may calculate the feature and then perform a classification to determine whether the subject suffers from CSR. The Cheyne-Stokes detection module may also output a report after calculating and classifying the raw features. More than one feature can also be classified in order to determine whether the subject suffers from CSR.

Classification of the raw features may be accomplished by a variety of methods. Whilst in the forthcoming examples the raw features are classified using the specifically discussed methods the raw features may be classified using a variety of different methods.

Cycle Length Histogram

Calculating the cycle length histogram will be explained first. A cycle length histogram is formed in order to characterize the distribution of the cycle lengths during a CSR period. The cycle length histogram gathers the cycle length data for a cluster of apneas/hypopneas during the CSR period and, based on its length, associates each cycle with one of a plurality of bins, effectively dividing the data into bins to evaluate the frequency of potential cycle lengths. Each bin may be identified by a midpoint and a width. The midpoints of the bins can be spaced equally or varied according to the density of data. In one example the bin midpoints are spaced evenly from 5 seconds to 105 seconds with a bin width of 10 seconds (e.g., discrete bins are formed having midpoints at 5, 15, 25, 35, . . . , 105). It will be understood, however, that the bin midpoints and bin widths can be varied as desired. For example, the bin width can be set at 3 seconds, 5 seconds, 10 seconds or 15 seconds. Additionally, histogram may include bins of varying widths according to the density of the data.

Each cycle from the cluster of the CSR period (e.g., those identified prior to reaching the time-out threshold) is evaluated and placed in the corresponding bin. The system immediately indicates a "provisional" or "possible" CSR period when an apnea or hypopnea occurs and such a provisional CSR period continues up until a cycle length reaches a time-out threshold. The fact that the cycle length timer reaches a time-out threshold indicates that two adjacent apneas and/or hypopneas are sufficiently far apart to indicate that the patient has returned to normal breathing. Such an event signals the end of the current provisional CSR period. The count for the time-out threshold starts every time the patient takes a spontaneous breath, but returns to 0 when an apneic period is identified. This threshold is reached only if no apneic period is encountered during a predetermined period. This time-out threshold predetermined period may be set to any duration of time as desired. For example, the time-out threshold may be set to 3, 4, 5 or 6 minutes as desired. In the described example, the time-out threshold is set to 3 minutes.

Figure 3:
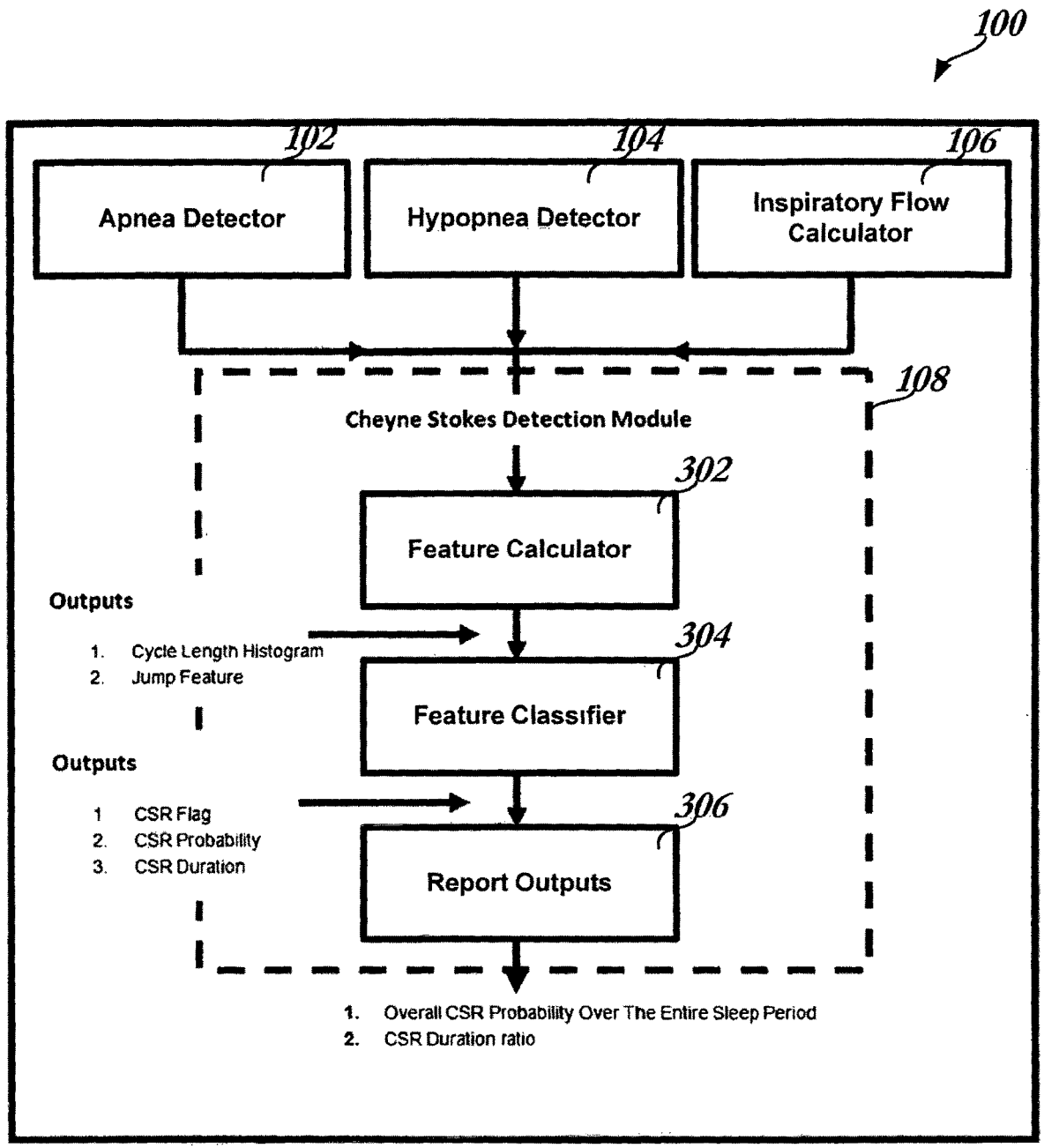
FIG. 3 is an extended structural diagram of the CSR detector of FIG. 1, wherein the detection module is presented by its components and their outputs.

FIG. 3 is a flow chart that illustrates the components and the outputs associated with the underlying calculations of the CSR probability. The calculation utilizes apnea status and apnea duration from the apnea detector, the hypopnea status and hypopnea duration from the hypopnea detector and the inspiratory peak flow from the inspiratory flow calculator.

Figure 4:
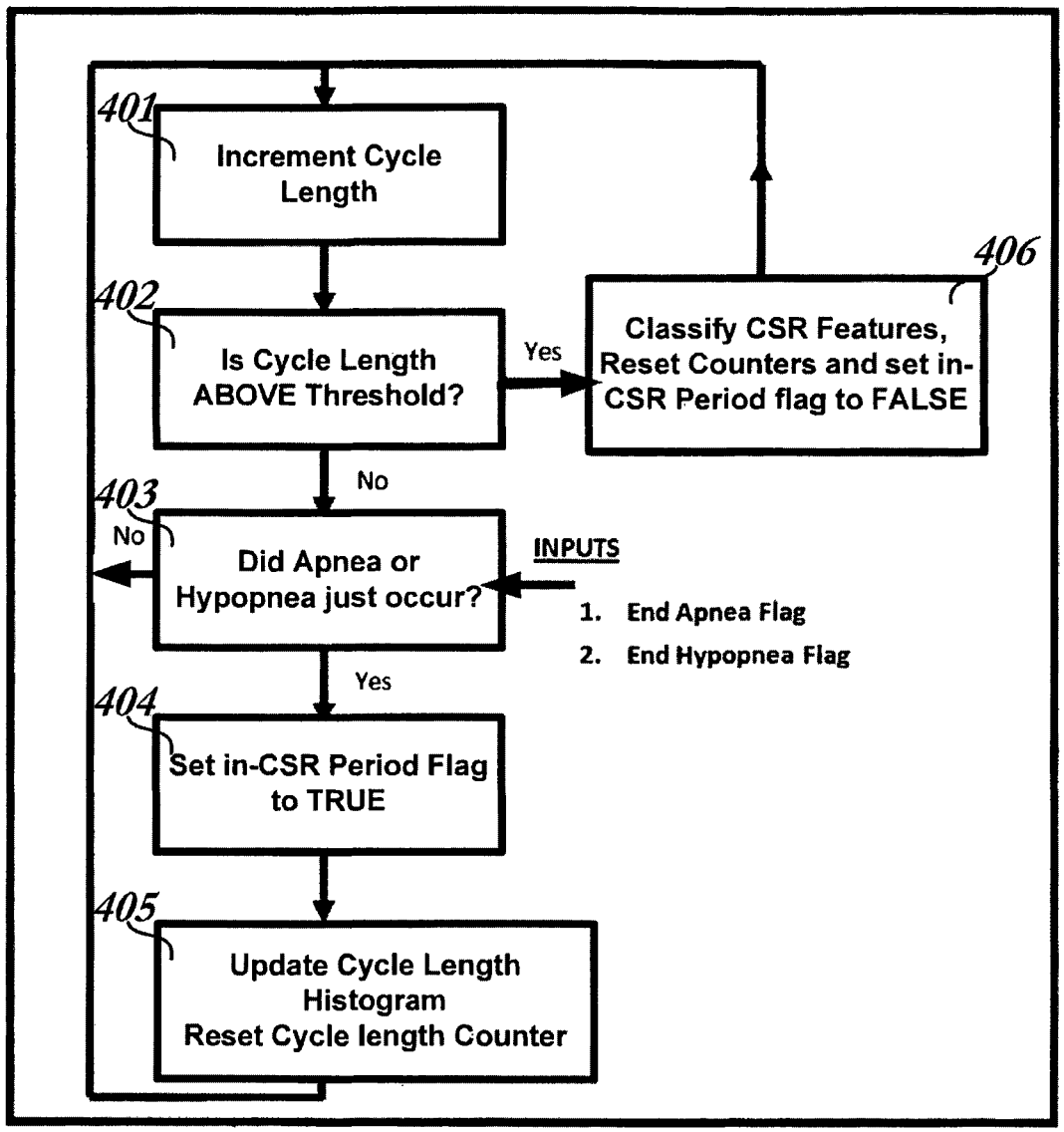
FIG. 4 is an example flow chart of a process for deriving one or more features that may be assessed in order to detect CSR in some embodiments.

FIG. 4 shows the process of classifying the CSR features during an in-CSR period. The shown cyclical process that characterizes each cycle length begins by incrementing the cycle length counter in step 401. The cycle length is then compared, in step 402, to a predetermined threshold, which in this case is the time-out threshold discussed above. The threshold may have a constant value or may be empirically trained. If the cycle length is above the predetermined threshold, the CSR features (e.g., cycle length histogram and corresponding shape feature) are classified, the cycle length counter, the cycle length histogram and the shape feature counters are reset, and the in-CSR period flag is set to false in step 406. The cycle length counter is restarted each time an apnea or hypopnea is encountered.

If, however, the cycle length is below the predetermined threshold the process continues in step 403 by examining whether an apnea or hypopnea has just occurred, i.e. by using the apnea detector 102 or the hypopnea detector 104, respectively. If true, in step 404 the in-CSR period flag, indicating the system enters a provisional CSR period, is set to true, the cycle length histogram is updated and the cycle length counter is reset to 0, which allows the next cycle length to begin. If an apnea or hypopnea has not occurred, the cycle returns to step 401 where the cycle length counter is incremented. By repeating this process, the various collected cycle lengths from the cluster of apneas and/or hypopneas are applied to bins.

Shape Feature Calculation

Figure 5A:
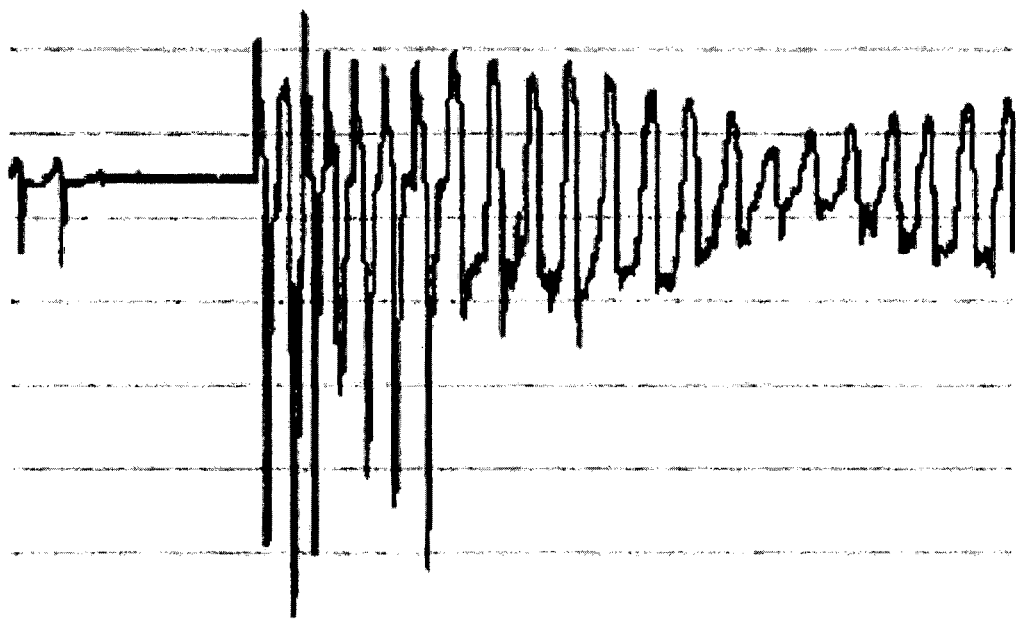
FIG. 5A shows the morphology of a respiratory flow waveform including an obstructive apnea.
Figure 5B:
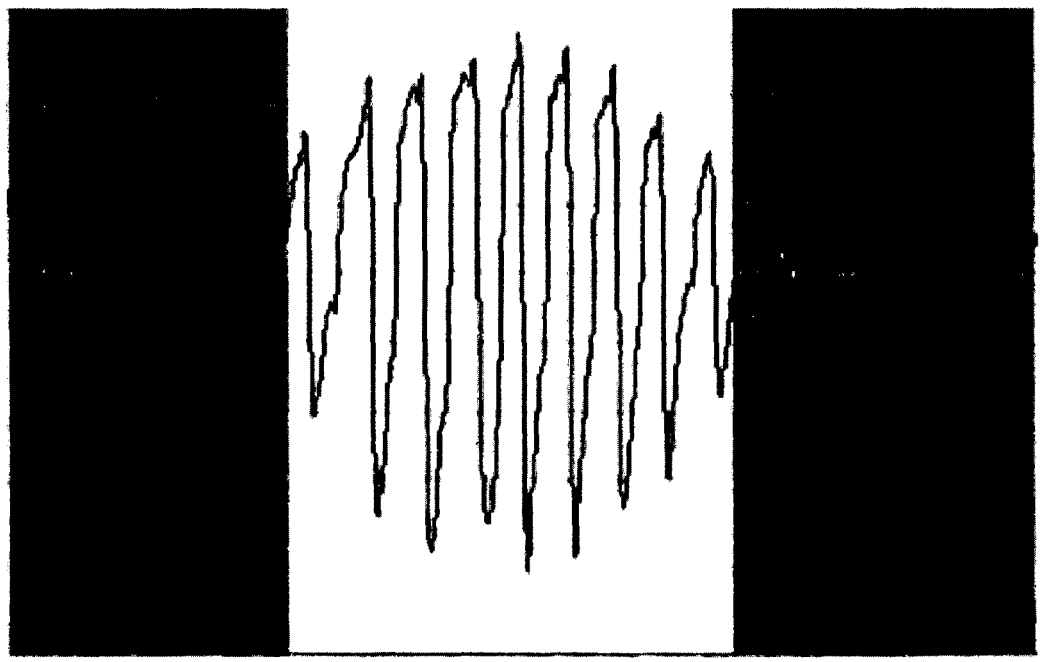
FIG. 5B shows the morphology of a respiratory flow waveform including a central apnea that may be indicative of CSR.

From the clusters of apneas and/or hypopneas, the shape feature may be similarly calculated. As described above, the shape feature is a measure used to describe the morphology of the flow waveform directly following an apnea or hypopnea. FIGS. 5A and 5B illustrate two different types of flow morphology. It will be understood that it is possible to classify and detect CSR using only one raw feature (e.g., only shape feature or only cycle length). In some embodiments, more than one raw feature may be evaluated and a combination of these can be used to produce a more accurate measure of the likelihood of CSR. Weighting coefficients may be applied to one or more of the features in such a case.

FIG. 5A shows a signal morphology after an obstructive apnea/hypopnea and FIG. 5B shows the signal morphology after a central apnea/hypopnea. As can be appreciated by comparing FIGS. 5A and 5B, the amplitude change in shape in the peak flow (the shape feature) is more gradual after a central event, when compared to the hyperapnea period following an obstructive event. This is related to breathing drive coming back slowly after central apneas. Because CSR is simply a period with a high density of central apneas/hypopneas, there will be a clear distinction in the flow morphology during a CSR event when compared to typical OSA.

There are numerous ways to calculate the shape feature. Peaks of the maximum and/or the minimum expiratory flow can be used in such calculation. In some embodiments, the product of the peak inspiratory flows and inspiratory tidal volumes, obtained from the inspiratory flow calculator, in between apneas/hypopnea is calculated and stored in a morphology vector (ShapeFeatVec). The shape feature can then be calculated by analyzing the relationship between the morphology vector and the reference vector (generated from an approximating function). As an example, the mean squared error (MSE) between the morphology vector and a reference vector could be used as a measure of this relationship. Any suitable approximating function may be used and there is no limitation of having only one approximating function. For example, the mean squared error may be calculated using a sine function and a cosine function and the two results can be used in conjunction by the feature classifier. Furthermore, not all the inspiratory peak flows and inspiratory tidal volumes during the hyperpnoea need to be used in calculating the shape feature. Also, any of the features of peak inspiratory flow and inspiratory tidal volume can be used individually for the detection of CSR. Optionally, other features of the flow signal can be implemented to characterize the morphology 'shape' (e.g. the inspiratory time).

In another embodiment, the morphology vector could be comprised of ventilation values between apnea and/hypopnea events (calculated by integrating the flow signal). The shape feature can then be calculated by analyzing the relationship between the resulting morphology vector and a reference vector (calculated by using an approximating function). As an example, the mean squared error (MSE)

between the morphology vector and the reference vector could be used as a measure of this relationship.

In one example, the shape feature may be calculated by employing approximating function b(x) for the current ShapeFeatVec, pf(y), as follows:

$$b(x)=\sin(\pi x), 0 \le x < 1$$

The shape feature is then obtained by calculating the mean square error (MSE) of b(x) and pf(y))

$$\text{Shape Feature} = \frac{1}{N}\sum_{i=1}^{N}(pf(y_i) - b(x_i))^2,$$

where N is the size of the peak flow vector, and pf(y) is the ShapeFeatVec.

Jump Feature

The jump feature 235, which is an example of the shape feature, may also be used to distinguish between obstructive apneas/hypopneas and central apneas/hypopneas. As can be appreciated by comparing FIGS. 5A and 5B, the amplitude change in the jump of peak flows (the jump feature) is more gradual after a central event, when compared to an equivalent hyperapnea period following an obstructive event. This is related to breathing drive coming back slowly after central apneas. Because CSR is simply a period with a high density of central apneas/hypopneas, there will be a clear distinction in the flow morphology during a CSR event when compared to typical OSA.

There are numerous ways to calculate the jump feature. Peaks of the maximum and/or the minimum inspiratory/expiratory flow can be used in such calculation. Alternatively inspiratory/expiratory tidal volumes, obtained from the inspiratory flow calculator in between apneas/hypopnea can be used. Alternatively, the ventilation values calculated between apneas and/or hypopneas may be stored in a morphology vector. The jump feature can then be calculated by any number of techniques which can extract the pattern as described above. As an example, the jump feature may be calculated by implementing the following steps:

1. Find the first peak in the morphology vector—Pmax
2. Find the point where a predetermined ratio to the peak is reached. The predetermined ratio may be a percentage of the peak, such as between 60% and 95%, preferably between 70 and 90%, in one instance—85% (the point where 85% of the peak is reached may be referred to as $P_{85}$).
3. Calculate the gradient between Pas and the first point ($P_0$) in the morphology vector
4. Apply any necessary scaling to the gradient and set that scaled gradient as the Jump Feature.

It must be noted that the above is only one type of example of calculating the jump feature. Any other method which attempts to quantify the return of breathing drive following an apnea can be used to calculate the jump feature. For example, the jump feature may also be calculated based not on respiratory flow, such as the one shown in FIG. 2, but on ventilation or tidal volume data. Because of the integrated nature of such functions, their profile can visually be compared to the breathing drive profile envelope 230. In this case, similarly to the above example, the jump feature may be derived by calculating the gradient of a line drawn between the peak of the envelope and a point from the envelope where a predetermined ratio to the peak is reached.

Duty Cycle

As previously mentioned, the duty cycle may be a ratio of the apnea length to the cycle length. For a typical Cheyne-Stokes patient, this duty cycle is expected to be approximately ⅓ (e.g., a 20-second apnea within a 60-second cycle length). Due to natural variation from patient to patient, the ratio may vary slightly. Mathematically the duty cycle is calculated as $$\text{Duty Cycle} = \frac{t_{apnea}}{t_{cycle}}$$

With the three raw features of cycle length histogram, shape feature and duty cycle calculated, a feature classifier can then be used to determine whether the patterns obtained correspond to CSR and if a CSR period has passed. Again, it may be noted that an individual feature, any combination or all of the raw features may be classified and used to detect CSR. This can be done by comparing the raw features with a set of thresholds (which may be determined empirically) that are representative of the CSR. Moreover, it will be understood that different methodologies may be used to classify the raw features to detect CSR. For example, as discussed herein the raw features may be transformed into a (0,1] probability space for detection. Alternatively, an algorithm may encode a Bayesian classification system, neural networks, clustering methods and/or any other machine learning algorithms to evaluate the raw features.

In one example the classification process may normalize the obtained raw features. This may be accomplished by using a transformation function and converting the raw features into a probability space where they can take any value between 0 and 1.

The shape feature transformation function may be expressed as:

$$J(x) = \begin{cases} 1, & x \le 0 \\ 0, & x > 1 \\ (\sin(-(x, \frac{\pi}{2})) + 1), & 0 < x \le 1 \end{cases},$$

where x is the raw shape feature.

In addition, the cycle length histogram peak location transformation function may be expressed as:

$$\text{NormHist} = \begin{cases} 0, & p < 35, p \ge 90 \\ 0.5, & 35 \le p < 45 \\ 1, & 45 \le p < 90 \end{cases},$$

where p is the midpoint of the bin with the highest peak from the cycle length histogram.

From the cycle length histogram, the power in the region of interest may also be calculated. The power may be calculated in one or more predetermined regions. The region of interest may be defined as the combination of bins which cover a specific set of cycle lengths. As previously discussed, the cycle length histogram has various bins spaced between 0 and 110 seconds. During a CSR period, it would be expected that the average cycle length would be between 40-90 seconds. Thus, in one example, the region of interest may be defined as the bins which cover cycle lengths between 40 and 90 seconds.

A histogram power transformation function may be calculated in various manners. In one example, the power in the region of interest is calculated from the cycle length histogram by first calculating p, the midpoint of the bin with the maximum count and pCount, the counts in that bin. Next, the process calculates p2, the midpoint of the bin with $2^{nd}$ highest count and p2Count, the counts in that bin. The power, C(p), is calculated as follows:

$$C(p) = \begin{cases} 0, & p < 35 \\ \sqrt{(pCount^2 + p2Count^2)}, & 35 \leq p \leq 90, p2 \leq 35, p2 \geq 90 \\ pCount + p2Count, & 35 \leq p < 90, 35 < p2 < 90 \end{cases}$$

Calculating CSR Probability

The CSR probability, CSRprob, may then be calculated as the product of the Shape Feature J(x), the histogram power, C(p), and the duty cycle:

$$CSRprob = \left\{ \frac{A \cdot J(x) + B \cdot C(p), 0.2 \leq DutyCycle \leq 0.7}{0, \text{Otherwise}} \right\}$$

In the calculation above, A and B are constants which may be trained. These constants can range across any real number, but may be set to a value between 0 and 1. For the sake of illustration, the value of A may be set to 0.3 and the value of B may be set to 0.7.

For each CSR period, the CSR_FLAG is set to TRUE if the CSRprob>0.5 and the CSR_PERIOD_TIMER is greater than a predetermined period referred to as a MIN_CSR_PERIOD. This period is associated with a general requirement to only qualify a period including apneas and hypopneas as a CSR period if it lasts longer than a predetermined length of time. The MIN_CSR_PERIOD may be predefined to have any clinically accepted figure that is empirically determined to ensure detected CSR event is not too short to be considered CSR. In one example the MIN_CSR_PERIOD may be 900 seconds.

It may be appreciated that the above formula allow for weighting of the morphology-related shape feature and the time-based histogram to balance the contribution of each of these features, as required.

In the evaluating step 406, if CSRprob>0.5 and the MIN_CSR_PERIOD has not elapsed, then CSR_FLAG is set to FALSE. If CSRprob<0.5 CSR_FLAG is also set to FALSE. The CSR duration of each period is taken from the value of CSR_PERIOD TIMER at the end of the period.

Having calculated CSRprob for a given CSR period, the CSR probability for the entire sleep period may also be calculated such as from multiple CSR periods. In at least some examples, the overall CSR probability for the entire sleep period may be calculated by processing the CSR probability for each flagged CSR period, such as by identifying CSR_FLAG=TRUE periods. In one example, this can be performed by averaging, via a simple arithmetic mean, the CSR probability for each flagged CSR period to obtain the overall CSR probability during the entire sleep period.

Another CSR Probability calculation may involve using HistPower and the Shape Feature J(x). In this case the CSRprob calculation is performed as follows:
1. For each J(x) and C(p) calculate D(x,p) and proceed to step 2 i. $D(x,p) = 1 - \sqrt{((1-C(p))^2 * (1-J(x))^2)}$.

2.
    i. IF 1−D(x,p)≤0.3, then set

CSRprob=D(x,p)

ii. ELSE proceed to step 3

3. IF 1−D(x,p)>0.3
    i. IF C(p) is greater than equal to 0.5

CSRprob=(C(p)+(D(x,p)))/1+(D(xp))

ELSE
    ii. CSRprob=0

Figure 6:
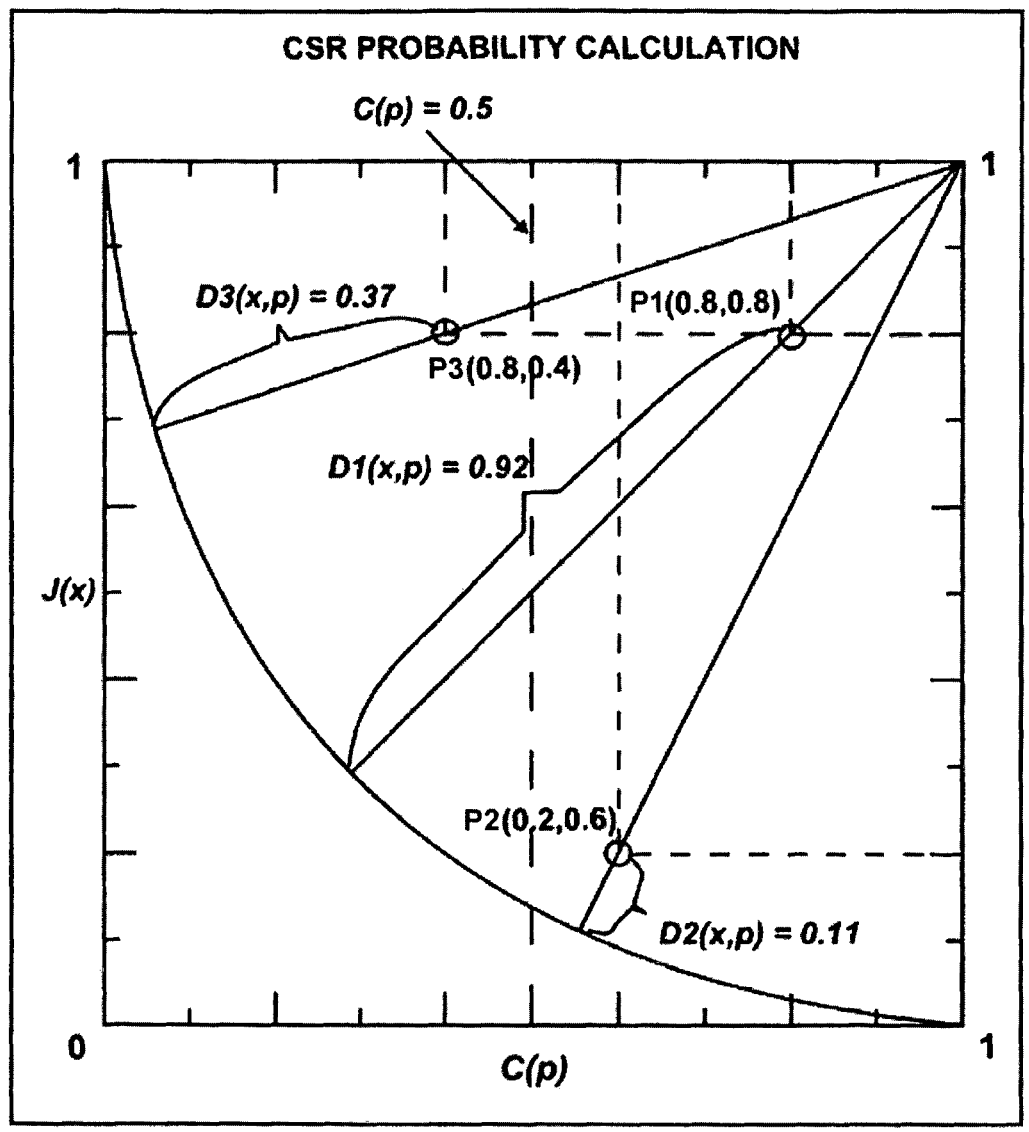
FIG. 6 shows several examples of calculated CSR probabilities.

FIG. 6 illustrates example cases visualized by three points P1, P2 and P3, located on different radiuses extending from a central point where the C(p)=1, the J(x)=1 and the CSR prob.=1.

Point P1
C(p)=0.8; J(x)=0.8; D1(x,p)=0.92
Since 1−D(x,p)≤0.3, the CSRprob is simply taken as D(x,p)=0.92

Point P2
C(p)=0.6; J(x)=0.2; D2(x,p)=0.11
Since 1−D(x,p)>0.3 AND C(p)≥0.5, the

CSRprob=(C(p)+(D(x,p)))/1+(D(xp))=0.56

Point P3
C(p)=0.4; J(x)=0.8; D3(x,p)=0.37
Since 1−D(x,p)>0.3 AND C(p)<0.5, CSRprob=0

In another example, the classification process may normalize any of the obtained raw features such as the shape feature (e.g., jump feature) and the cycle length histogram by using a transformation function and converting the raw features into a probability space where they can take any value between 0 and 1. Following this, statistical analysis methods can be applied to classify the feature and thence derive a CSR Probability.

In one embodiment, the statistical analysis could involve using non-parametric analysis to classify the transformed feature. More specifically, histograms may be formed and processed to classify the features. It must be noted that histograms are only one of many techniques which can be used to analyze the statistics of the transformed features. As an example, the following steps may be followed to derive a CSR Probability:
1. Distribute the transformed features in bins and form a histogram (e.g., shape feature or jump feature)
2. Calculate the power of the histograms in the region (0.5,1.0)
3. If the power of all the histograms is greater than a set threshold (eg. 0.5), then the CSR probability (CSRprob) is taken as the maximum of the histogram powers.

The CSR_FLAG is then set to TRUE if the CSRprob>0.5 and the CSR_PERDIOD_TIMER is greater than the MIN_CSR_PERIOD. If CSRprob>0.5 and the MIN_CSR_PERIOD has not elapsed, then set CSR_FLAG to FALSE. If CSRprob<0.5 then set CSR_FLAG to FALSE.

It can be seen from FIG. 6 that in the above described steps 1 to 3, the threshold value of 0.3 is somewhat arbitrarily chosen to indicate a range that is in the vicinity of the central point. However other values can also be chosen, say within the range of 0.1 to 0.6, and definitely <1.

Figure 7:
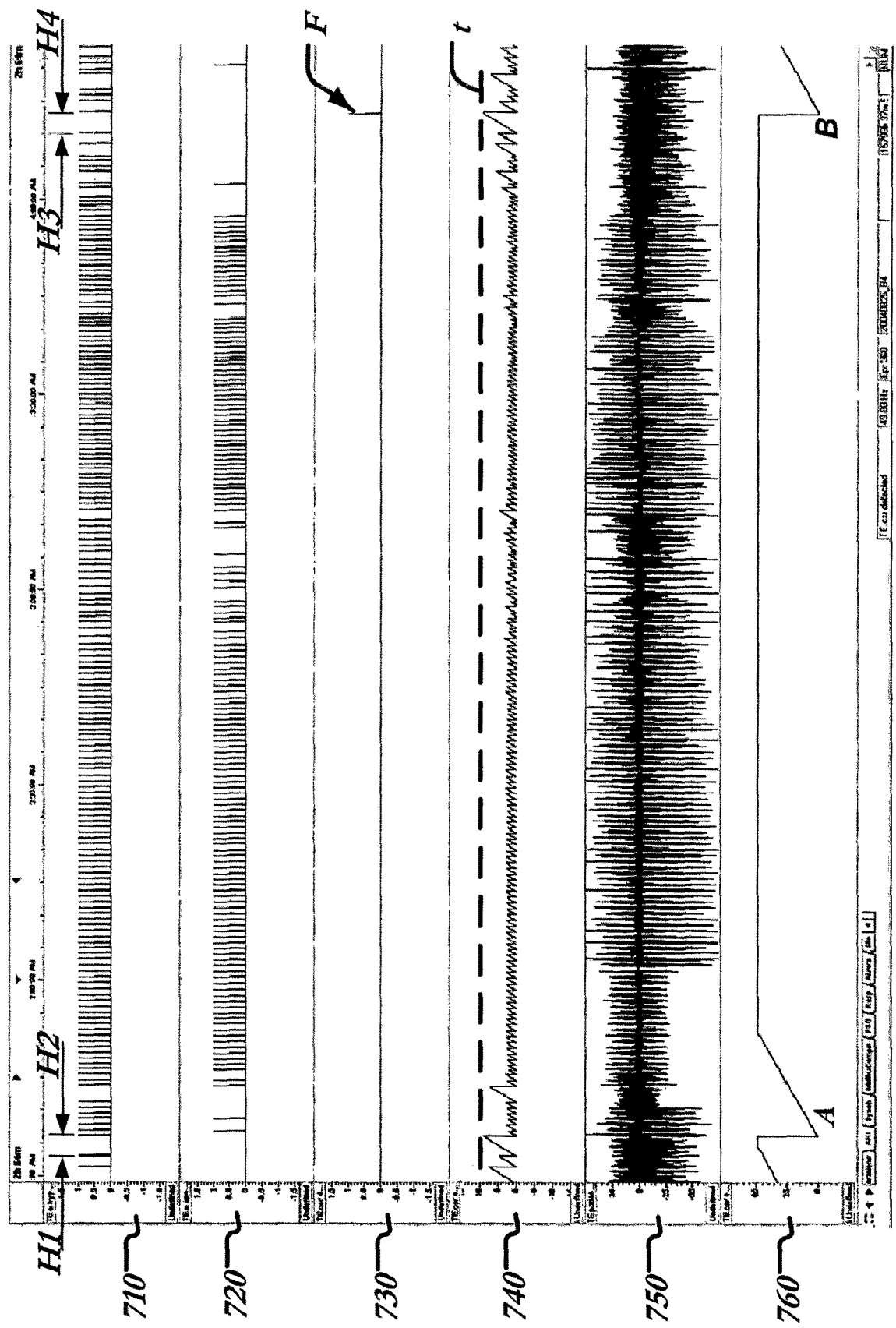
FIG. 7 shows a polysomnographic record of a typical CSR period, including various features involved in the detection of a CSR period.

FIG. 7 is a polysomnographic record of a typical CSR period, showing a number of features taking part in the detection of a CSR period on a common time axis. The CSR period illustrated in the figure extends over two hours. Panel 750 of the polysomnographic record displays a signal representing the patient's respiratory flow. Panel 710 contains a hypopnea flag signal that indicates the occurrence of hypopnea, while panel 720 shows an Apnea flag signal that indicates the occurrence of apnea. Panel 740 displays a signal representing the CSR CYCLE_LENGTH_TIMER discussed with reference to FIG. 4, which is restarted from zero when an apnea or a hypopnea occurs. Panel 760 displays a signal representing the CSR_PERIOD_TIMER indicating that the system is in-CSR period, whilst panel 730 contains the CSR_FLAG signal which provides a notification that a CSR has been positively detected.

The CSR_PERIOD_timer starts counting when an apnea or hypopnea occurs and keeps counting (its value keeps accumulating, even though the value displayed in panel 760 is clipped) until the CYCLE_LENGTH_TIMER reaches the CSR Time-Out threshold. At this stage, the CSR Flag is set to TRUE if the CSRProb for the calculated period is greater than 0.5 AND the CSR_PERIOD_TIMER is greater than MIN_CSR_PERIOD. In the case of the scenario illustrated in FIG. 6, the CSRProb=0.76 and the value of the CSR_PERIOD_TIMER is greater than MIN_CSR_PERIOD so the CSR_FLAG is set, indicating the detection of a valid CSR period.

The provisional in-CSR period extends in FIG. 7 between the points A and B. The starting point A is triggered when the time between the two apnoetic events, in this case the hypopneas H1 and H2, is sufficient to allow the CSR CYCLE_LENGTH_TIMER to reach the MIN_CSR_PERIOD time threshold, indicated by dotted line t. The density of apneas and hypopneas in panels 710 and 720 is such that the CSR CYCLE_LENGTH_TIMER in panel 740 keeps getting restarted and only reaches the MIN_CSR_PERIOD again at point B, which is allowed by a similarly large distance between hypopneas H3 and H4. At this point the CSR features are classified. As the evaluation of the CSRProb returns 0.76 and the CSR_PERIOD_TIMER has counted for about two hours and is well above the MIN_CSR_PERIOD, the CSR_FLAG is set as shown by "F".

Other methods of processing may include introducing weighting coefficients for the CSR probability, CSRprob, for each period. Such weighting coefficients may, for example, depend on the duration or the average duty cycle of the respective CSR Period. Knowing the expected duration and expected duty cycle of a typical CSR period, the CSRprob for one or more periods may be weighted to reflect the increased likelihood of CSR if the duration and/or duty cycle is close to the expected values.

Finally, a CSR duration ratio may be calculated as the ratio between the combined duration of all flagged CSR periods and the total sleep time. The overall CSR probability and the CSR duration ratio may be indicative of the amount and clinical significance of the detected CSR. The combined durations, the number of CSR flags for the night, the duration of each CSR period, as well as the calculated CSR probability associated with each of these periods can then be used to indicate the probability and severity of CSR such as by outputting the data to an LCD or other output device.

Accordingly, embodiments of the present technology may include a device or apparatus having one or more processors to implement particular CSR detection and/or training methodologies such as the classifiers, thresholds, functions and/or algorithms described in more detail herein. Thus, the device or apparatus may include integrated chips, a memory and/or other control instruction, data or information storage medium. For example, programmed instructions encompassing such detection and/or training methodologies may be coded on integrated chips in the memory of a device or apparatus, such as a flow generator. Such instructions may also, or alternatively, be loaded as software or firmware using an appropriate data storage medium. With a controller having such a processor, the respiratory treatment device for generating a flow can also be used for detection of CSR. The processor may control the assessment of a CSR occurrence or probability as described in the embodiments discussed in more detail herein. In some embodiments, the processor control instructions may be contained in a computer readable recording medium as software for use by a general purpose computer so that the general purpose computer may serve as a specific purpose computer according to any of the methodologies discussed herein upon loading the software into the general purpose computer.

Figure 8:
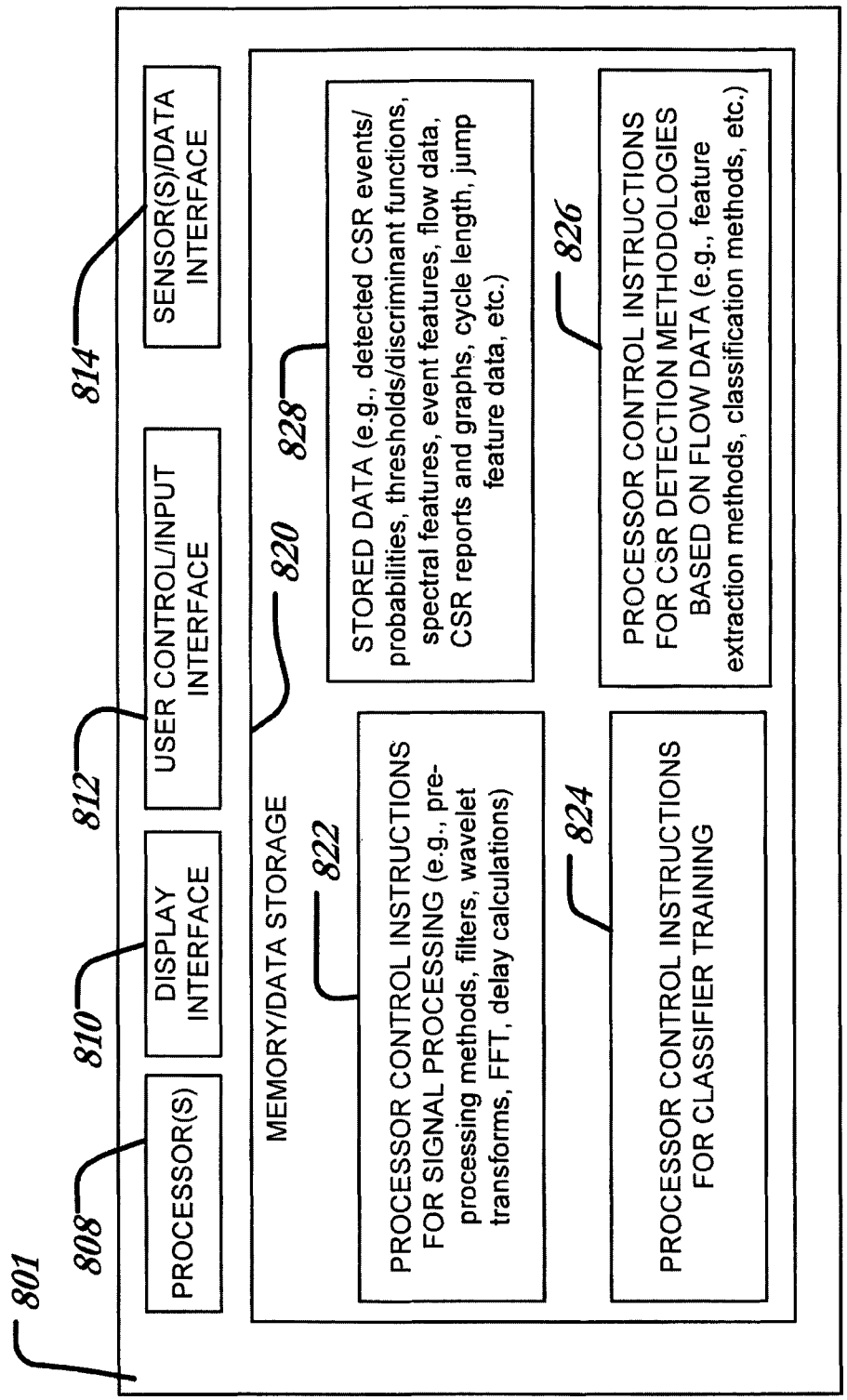
FIG. 8 is a schematic diagram of an example CSR detection and/or training apparatus according to the present technology.

A schematic diagram of example architecture of a CSR detection device (or apparatus or an equivalent general purpose computer) according to the present technology is illustrated in FIG. 8. In the illustration, the CSR detection device 801 may include one or more processors 808. The device may also include a display interface 810 to output CSR detection reports, results or graphs as described herein such as on a monitor or LCD panel (not shown). A user control/input interface 812, for example, for a keyboard, mouse, etc. may also be provided to activate the methodologies described herein. The device may also include a sensor or data interface 814 for receiving data such as programming instructions, oximetry data, flow data, respiration signal data, etc. The device may also typically include memory/data storage components. These may include processor control instructions for signal processing (e.g., re-processing methods, filters, at 822 as discussed in more detail herein. They may also include processor control instructions for classifier training methodologies at 824. They may also include processor control instructions for CSR detection methodologies based on respiration data (e.g., feature extraction methods, classification methods, etc.) at 826 as discussed herein. Finally, they may also include stored data 828 for these methodologies such as detected CSR events/probabilities, thresholds/discriminant functions, cycle length histogram features, event features, flow data, CSR reports, mean resaturation duration, resaturation periods, etc.

Figure 9:
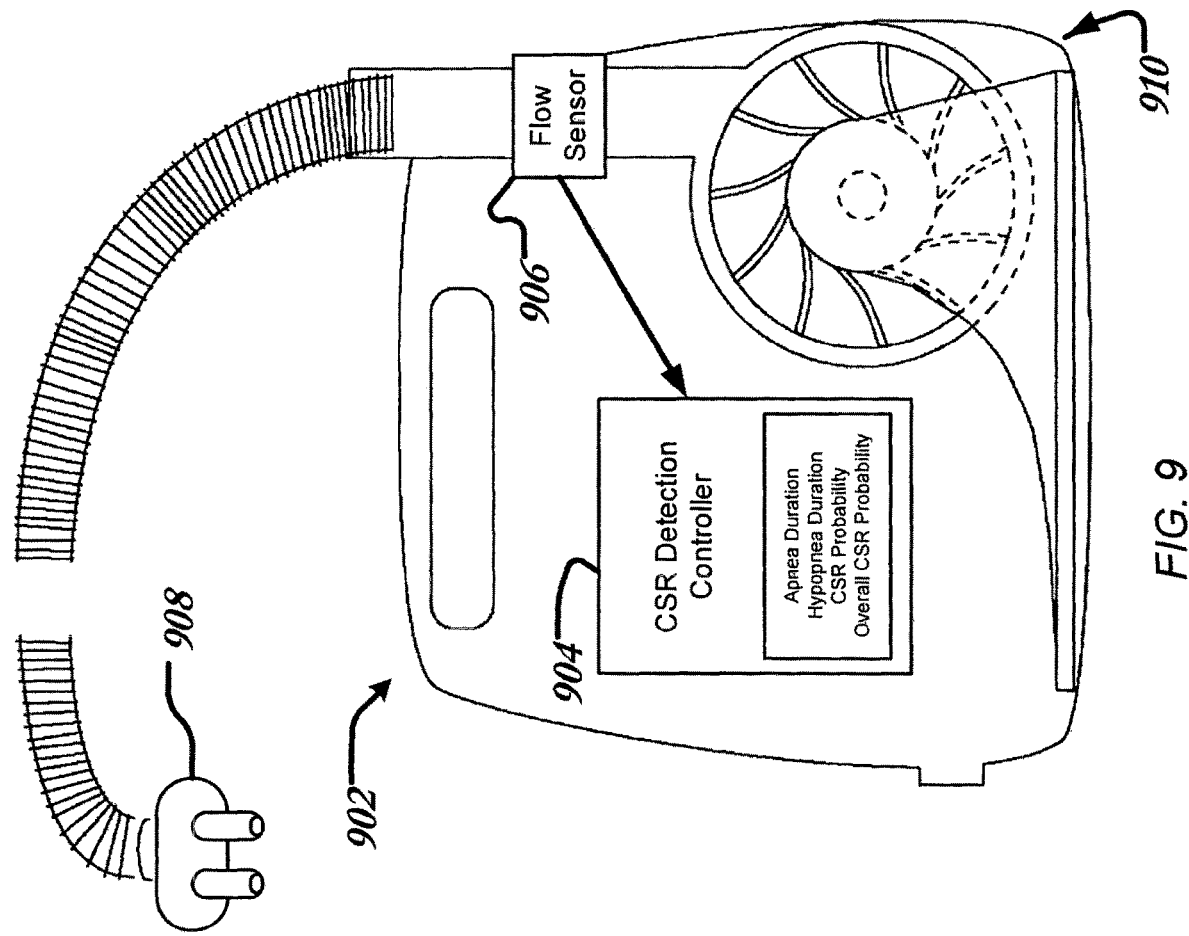
FIG. 9 shows an example CSR detection apparatus of the present technology with an optional flow sensor and a flow generator.

As illustrated in FIG. 9, embodiments of the present technology may include a CSR detection device or apparatus having a controller 904 that may have one or more processors to implement particular CSR detection methodologies such as the algorithms described in more detail herein. Thus, the device or apparatus may include integrated chips, a memory and/or other control instruction, data or information storage medium. For example, programmed instructions encompassing such detection methodologies may be coded on integrated chips in the memory of the device or apparatus to form an application specific integrated chip (ASIC).

Such instructions may also, or alternatively, be loaded as software or firmware using an appropriate data storage medium. With such a controller or processor, the device can be used for processing data from a flow signal. Thus, the processor may control the assessment of a CSR occurrence or severity as described in the embodiments discussed in more detail herein based on measured and recorded respiratory flow data from a prior sleep session. Alternatively, the detection may be performed during a sleep session contemporaneously with the measuring of a respiratory flow signal. Thus, in some embodiments, the device or apparatus itself may optionally be implemented with a flow sensor 706 for measuring a respiratory flow signal for use with the implemented methodologies. For example, flow to or through a nasal cannula 708 or mask may be measured using a pneumotachograph and differential pressure transducer or similar device such as one employing a bundle of tubes or ducts to derive a flow signal. Optionally, a flow signal may be inferred from other sensors, such as, a motor current sensor as described in PCT/AU2005/001688 filed on Nov. 2, 2005, the entire disclosure of which is incorporated herein by cross reference.

By way of further example, the CSR detection device may be implemented with a control methodology to respond to detected CSR as a respiratory treatment apparatus. For example, as illustrated in FIG. 9, a detection device may be optionally implemented with a flow generator such as a servo controlled blower with suitable sensors for such control (e.g., a pressure sensor). A respiratory treatment or pressure therapy regime, such as a therapeutic pressure level associated with CPAP treatment, may be delivered by the controller of the device. Such therapeutic pressure levels may be automatically adjusted in response to the detection of CSR conditions as described herein. For example, pressure levels may be increased by a specified amount, or varied otherwise, upon detection of CSR. Optionally, it may be increased proportionally as a function of a detected CSR severity.

While the present technology has been explained in terms of a method (e.g. a sequential process or algorithm) it may be understood that the process or algorithm can be carried out using a non-linear, non-sequential, or non-staged process, or the order of the process may be changed. While the described technology relates to an entire process, aspects of the technology may relate to only a subset of that process.

While the technology has been described in connection with what are presently considered to be practical and preferred examples, it is to be understood that the technology is not to be limited to the disclosed examples, but on the contrary, is intended to cover various modifications and equivalent arrangements included within the spirit and scope of the technology.

The invention claimed is:

1. A method implemented by a processor for detecting a presence of Cheyne-Stokes respiration from a respiration signal generated by a respiration sensor, the method comprising:
   accessing data representative of the respiration signal, the accessed data comprising respiratory data;
   assessing the accessed data to detect apnea and/or hypopnea events;
   evaluating the respiratory data directly following the detected events to estimate a shape feature representing a change in the respiratory data;
   generating a cycle length histogram based on the detected events, wherein the cycle length histogram includes a plurality of bins associated with a plurality of cycle lengths, each cycle length of the plurality being determined from the detected apnea and/or hypopnea events;
   detecting an incident of Cheyne-Stokes respiration based on the cycle length histogram and the estimated shape feature, wherein detecting the incident of Cheyne-Stokes respiration comprises calculating power over a combination of bins covering a select set of cycle lengths; and
   responding to the detection of an incident of Cheyne-Stokes respiration, the responding comprising controlling an adjustment of a therapeutic pressure delivered by a respiratory treatment apparatus.

2. The method of claim 1, wherein each of the plurality of bins has a midpoint and a bin width.

3. The method of claim 1, wherein the plurality of bins are evenly spaced.

4. The method of claim 1 wherein assessing the accessed data to detect apnea and/or hypopnea events comprises determining a duration of each event.

5. The method of claim 1, wherein the shape feature represents at least one of a rise and a fall of a breathing drive of a patient.

6. The method of claim 1, wherein the shape feature is a jump feature.

7. The method of claim 6, wherein the jump feature is calculated by selecting a first peak of the respiratory data, selecting a second peak at a predetermined ratio of the first peak and calculating a gradient between the first peak and the second peak.

8. The method of claim 7, further comprising scaling the gradient between the first peak and the second peak.

9. The method of claim 5, wherein the shape feature is estimated by fitting an approximating function to the respiratory data.

10. The method of claim 1, wherein the respiratory data comprises values of respiratory flow peaks or values of tidal volumes.

11. A method implemented by a processor for detecting a presence of Cheyne-Stokes respiration from a respiration signal generated by a respiration sensor, the method comprising:
    accessing respiratory flow data representative of the respiration signal;
    assessing the accessed respiratory flow data to detect apnea and/or hypopnea events;
    determining a cycle length histogram based on the detected events, wherein the cycle length histogram includes a plurality of bins associated with a plurality of cycle lengths, each cycle length of the plurality being determined from the detected apnea and/or hypopnea events;
    evaluating peaks in the flow data directly following the detected events to estimate a shape feature representing a change in the peaks of the flow data;
    detecting an incident of Cheyne-Stokes respiration based on the cycle length histogram and the shape feature, wherein detecting the incident of Cheyne Stokes respiration comprises calculating power over a combination of bins covering a select set of cycle lengths; and
    responding to the detecting of an incident of Cheyne-Stokes respiration, the responding comprising controlling an adjustment to a therapeutic pressure delivered by a respiratory treatment apparatus.

12. The method of claim 11, further comprising normalizing the cycle length histogram and the shape feature by converting them into a probability space with a range of values between 0 and 1.

13. The method of claim 11, wherein assessing the accessed respiratory flow data to detect apnea and/or hypopnea events comprises calculating duration of at least one apneic period and at least one cycle length and further comprising calculating a duty cycle based on the duration of the at least one apneic period and the at least one cycle length.

14. The method of claim 11, wherein detecting the incident of Cheyne-Stokes respiration comprises determining a Cheyne-Stokes respiration probability using the shape feature, cycle length and the power.

15. The method of claim 14, further comprising determining an overall Cheyne-Stoke respiration probability over an entire sleep period by combining weighted Cheyne-Stokes respiration probability for multiple selected periods.

16. The method of claim 11, wherein the shape feature represents at least one of a rise and a fall of a breathing drive of a patient.

17. The method of claim 1 wherein detecting of the incident of Cheyne-Stokes respiration comprises applying the estimated shape feature and the cycle length histogram to a classifier implemented by the processor.

18. The method of claim 1 wherein the controlling an adjustment of a therapeutic pressure delivered by a respiratory treatment apparatus further comprises automatically controlling a blower of a flow generator in response to the detecting of the incident of Cheyne-Stokes respiration that is based on the cycle length histogram and the estimated shape feature.

19. The method of claim 1 wherein calculating power evaluates a histogram power transformation function that determines a first count of a first bin of the plurality of bins as a maximum count and a second count of a second bin of the plurality of bins as a second highest count, and adds the first count and second count when midpoints of first bin and the second bin are each within a predefined range.

20. The method of claim 19 wherein the histogram power transformation function determines a square root of an addition of a square of the first count and a square of the second count when a midpoint of the first bin is within the predefined range and a midpoint of the second bin is outside the predefined range.

21. The method of claim 11 wherein detecting of the incident of Cheyne-Stokes respiration comprises applying the estimated shape feature and the cycle length histogram to a classifier implemented by the processor.

22. The method of claim 11 wherein the controlling the adjustment to a therapeutic pressure delivered by a respiratory treatment apparatus further comprises automatically controlling a blower of a flow generator in response to the detecting of the incident of Cheyne-Stokes respiration that is based on the cycle length histogram and the estimated shape feature.

23. The method of claim 11 wherein calculating power evaluates a histogram power transformation function that determines a first count of a first bin of the cycle length histogram as a maximum count and a second count of a second bin of the cycle length histogram as a second highest count, and adds the first count and second count when midpoints of first bin and the second bin are each within a predefined range.

24. The method of claim 23 wherein the histogram power transformation function determines a square root of an addition of a square of the first count and a square of the second count when a midpoint of the first bin is within the predefined range and a midpoint of the second bin is outside the predefined range.

25. The method of claim 1 wherein the responding further comprises generating and displaying an incident report upon a monitor.

26. The method of claim 11 wherein the response further comprises generating and displaying an incident report upon a monitor.

* * * * *

UNITED STATES PATENT AND TRADEMARK OFFICE
CERTIFICATE OF CORRECTION

PATENT NO. : 10,863,949 B2
APPLICATION NO. : 14/374761
DATED : December 15, 2020
INVENTOR(S) : Jeffrey Peter Armitstead and Dinesh Ramanan It is certified that error appears in the above-identified patent and that said Letters Patent is hereby corrected as shown below:

On the Title Page

Delete "26 Claims" and insert --38 Claims--

In the Claims

After Claim 26, the following claims should be added:
27. An apparatus for detecting a presence of Cheyne Stokes respiration from a respiration signal generated by a respiration sensor, the apparatus comprising:
    a memory for storing respiratory data associated with the respiration signal; and
    a processor, coupled with the memory, the processor being configured
        (a) to assess the respiratory data to detect apnea and/or hypopnea events,
        (b) to evaluate the respiratory data directly following the detected events to estimate a shape feature representing change in the respiratory data,
        (c) to generate a cycle length histogram based on the detected events, wherein the cycle length histogram includes a plurality of bins associated with a plurality of cycle lengths, each cycle length of the plurality being determined from the detected apnea and/or hypopnea events,
        (d) to detect an incident of Cheyne Stokes respiration based on the cycle length histogram and the estimated shape feature, wherein to detect the incident of Cheyne Stokes respiration comprises calculation of power over a combination of bins covering a select set of cycle lengths, and
        (e) to generate a response to the detection of an incident of Cheyne-Stokes respiration, the response comprising an adjustment to therapeutic pressure delivered by a respiratory treatment apparatus.

28. The apparatus of claim 27, wherein the shape feature represents at least one of a rise and a fall of a breathing drive of a patient.

29. The apparatus of claim 27, wherein the processor is configured to evaluate at least one of values of respiratory flow peaks, ventilation or tidal volumes of the respiration signal.

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*

30. An apparatus for detecting a presence of Cheyne Stokes respiration from a respiration signal generated by a respiration sensor, the apparatus comprising:
   a memory for storing respiratory data associated with the respiration signal; and
   a processor, coupled with the memory, the processor being configured to:
      (a) assess the respiratory data to detect apnea and/or hypopnea events,
      (b) determine a cycle length histogram based on the detected events, wherein the cycle length histogram includes a plurality of bins associated with a plurality of cycle lengths, each cycle length of the plurality being determined from the detected apnea and/or hypopnea events,
      (c) evaluate peaks in the respiratory data directly following the detected events to estimate a shape feature,
      (d) detect an incident of Cheyne Stokes respiration based on the cycle length histogram and the shape feature, comprising calculation of power over a combination of bins covering a select set of cycle lengths, and
      (e) generate a response with the detected incident of Cheyne-Stokes respiration, the response comprising an adjustment to therapeutic pressure delivered by a respiratory treatment apparatus.

31. The apparatus of claim 30, wherein the processor is configured to assess the data to detect the apnea and/or hypopnea events by calculating a duration of at least one apneic period and at least one cycle length and the processor is further configured to calculate a duty cycle based on the duration of the at least one apneic period and the at least one cycle length.

32. The apparatus of claim 31, wherein the processor is configured to detect an incident of Cheyne Stokes respiration by calculating power over a combination of bins covering a select set of cycle lengths and determining a Cheyne Stokes respiration probability using the shape feature, cycle length and the power.

33. The apparatus of claim 30, wherein the shape feature represents at least one of a rise and a fall of a breathing drive of a patient.

34. An apparatus to detect CSR from a respiration signal generated by a respiration sensor, the apparatus comprising:
   a controller having at least one processor to access respiratory data representing the respiration signal, the controller being further configured to:
      (a) assess the respiratory data to detect apnea and/or hypopnea events,
      (b) determine a cycle length histogram based on the detected events, wherein the cycle length histogram includes a plurality of bins,
      (c) evaluate the respiratory data directly following the detected events to calculate a shape feature,
      (d) detect an incident of Cheyne Stokes respiration based on the cycle length histogram and the shape feature, and
      (e) generate a response to the detection of the incident of Cheyne-Stokes respiration, the response an adjustment to therapeutic pressure delivered by a respiratory treatment apparatus.

35. The apparatus of claim 34, wherein the respiratory data comprises respiratory flow, ventilation or tidal volume data and the calculation of the shape feature is based on values of at least one of the respiratory flow, ventilation and tidal volume data.

36. The apparatus of claim 34, further comprising a flow sensor, wherein the controller is further configured to determine the respiration signal with the flow sensor.

37. The apparatus of claim 36, further comprising:
 a flow generator configured to produce a breathable gas for a patient at a pressure above atmospheric pressure;
 wherein the controller is further configured to control the flow generator to produce the breathable gas according to a pressure therapy regime based on the detected apnea and/or hypopnea events.

38. The apparatus of claim 34, wherein the shape feature represents at least one of a rise and a fall of a breathing drive of a patient.